(12) United States Patent
Bollu et al.

(10) Patent No.: US 11,053,220 B2
(45) Date of Patent: Jul. 6, 2021

(54) PROCESS FOR 3-(4-METHYL-1H-IMIDAZOL-1-YL)-5-(TRIFLUOROMETHYL) ANILINE

(71) Applicant: Laurus Labs Ltd, Hyderabad (IN)

(72) Inventors: Ravindra Babu Bollu, Hyderabad (IN); Veera Narayana Bandlamudi, Hyderabad (IN); Vivek Kumar Kudirilla, Hyderabad (IN); Rambabu Vemula, Hyderabad (IN); Uma Maheswer Rao Vasireddi, Hyderabad (IN)

(73) Assignee: LAURUS LABS LTD, Hyderabad (IN)

( * ) Notice: Subject to any disclaimer, the term of this patent is extended or adjusted under 35 U.S.C. 154(b) by 0 days.

(21) Appl. No.: 16/954,936

(22) PCT Filed: Dec. 28, 2018

(86) PCT No.: PCT/IB2018/060680
§ 371 (c)(1),
(2) Date: Jun. 17, 2020

(87) PCT Pub. No.: WO2019/130254
PCT Pub. Date: Jul. 4, 2019

(65) Prior Publication Data
US 2020/0377475 A1 Dec. 3, 2020

(30) Foreign Application Priority Data
Jan. 1, 2018 (IN) .............................. 201841000048

(51) Int. Cl.
*C07D 233/61* (2006.01)
*C07D 401/14* (2006.01)

(52) U.S. Cl.
CPC .......... *C07D 401/14* (2013.01); *C07D 233/61* (2013.01)

(58) Field of Classification Search
CPC ........................... C07D 233/61; C07D 401/14
See application file for complete search history.

(56) References Cited

FOREIGN PATENT DOCUMENTS

CN 104592122 A 5/2015
WO WO 2006135640 A2 12/2006

OTHER PUBLICATIONS

International Search Report dated Apr. 26, 2019; International Application No. PCT/IB2018/060680; Dec. 28, 2018; 5 pages.
Written Opinion dated Apr. 26, 2019; International Application No. PCT/IB2018/060680; Dec. 28, 2018; 5 pages.

*Primary Examiner* — Brenda L Coleman
(74) *Attorney, Agent, or Firm* — Blank Rome LLP

(57) ABSTRACT

The present invention relates to an improved process for the preparation of 3-(4-methyl-1H-imidazol-1-yl)-5-(trifluoromethyl) aniline of Formula (I).

24 Claims, 1 Drawing Sheet

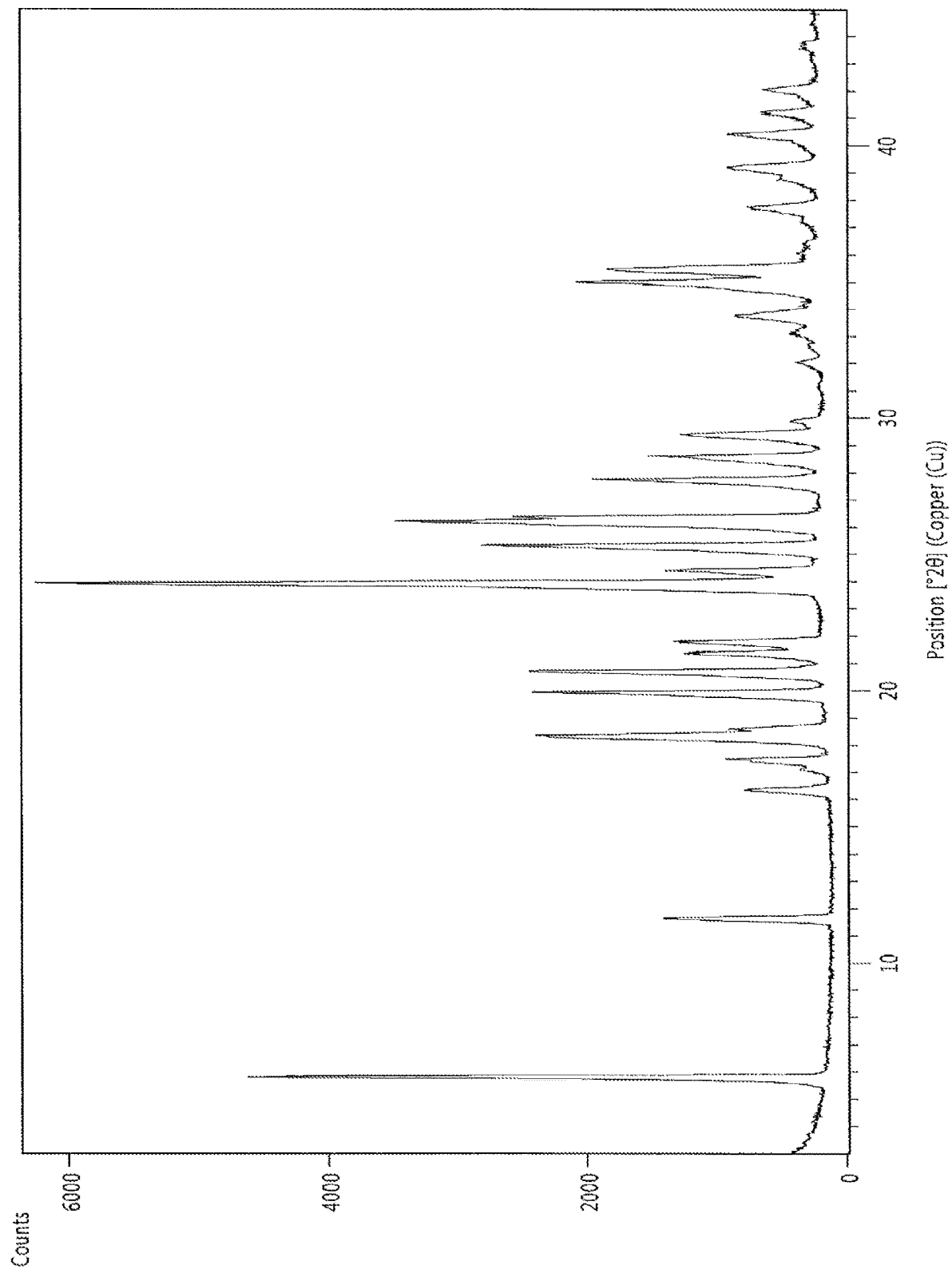

PROCESS FOR 3-(4-METHYL-1H-IMIDAZOL-1-YL)-5-(TRIFLUOROMETHYL) ANILINE

CROSS-REFERENCE TO RELATED APPLICATIONS

This application is a national phase application that claims the benefit of International Application PCT/IB2018/060680, filed on Dec. 28, 2018, which is based on and claims the benefit of Indian Provisional Application No. 201841000048, filed on Jan. 1, 2018, entitled "An Improved Process for 3-(4-methyl-1H-imidazol-1-yl)-5-(trifluoromethyl) aniline", the content of which are incorporated by reference herein.

FIELD OF THE INVENTION

The present invention relates to an improved process for the preparation of 3-(4-methyl-1H-imidazol-1-yl)-5-(trifluoromethyl) aniline of Formula (I).

BACKGROUND OF THE INVENTION 3-(4-methyl-1H-imidazol-1-yl)-5-(trifluoromethyl)aniline represented by the following structural Formula (I)

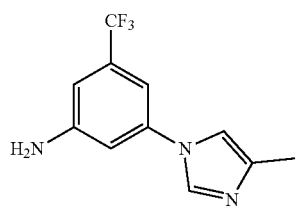

Formula (I)

which is an important intermediate useful in the preparation of nilotinib represented by the following structural Formula (II) or its pharmaceutically acceptable salts.

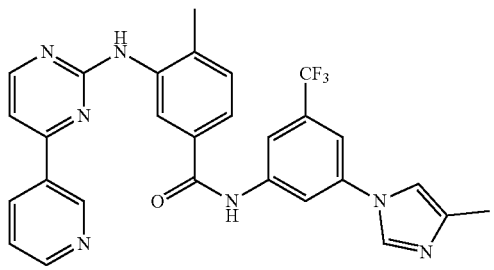

Formula (II)

Nilotinib is chemically known as 4-methyl-N-[3-(4-methyl-1H-imidazol-1-yl)-5-(trifluoromethyl)phenyl]-3[[4-(3-pyridinyl)-2-pyrimidinyl]amino]benzamide. Nilotinib is a small-molecule tyrosine kinase inhibitor, which is approved in the form of the hydrochloride monohydrate salt for the treatment of imatinib-resistant chronic myelogenous leukemia.

3-(4-methyl-1H-imidazol-1-yl)-5-(trifluoromethyl) aniline of Formula (I) and its use in the preparation of nilotinib of Formula (II) was first disclosed in PCT publication WO2004005281 ("the WO'281 publication") and the same was schematically represented by the following scheme:

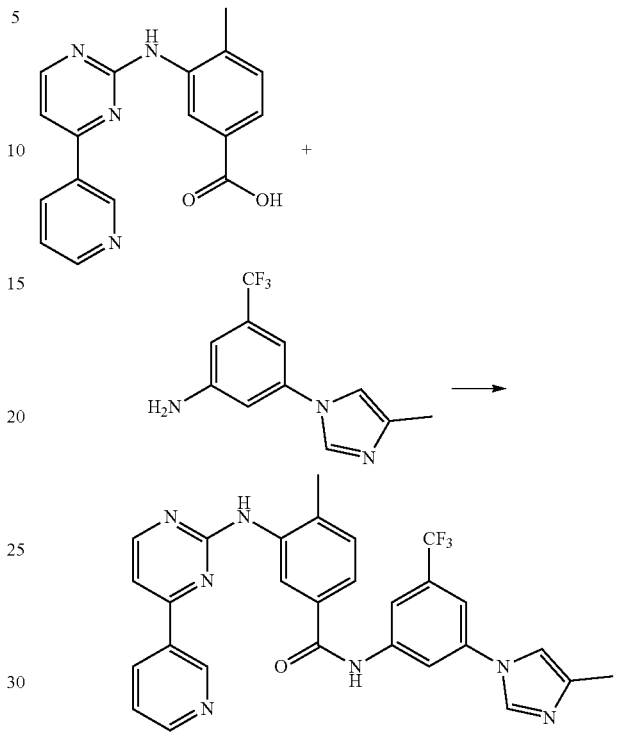

The said WO'281 publication also discloses a process for the preparation of 3-(4-methyl-1H-imidazol-1-yl)-5-(trifluoromethyl)aniline of Formula (I), which is schematically represented by the following scheme:

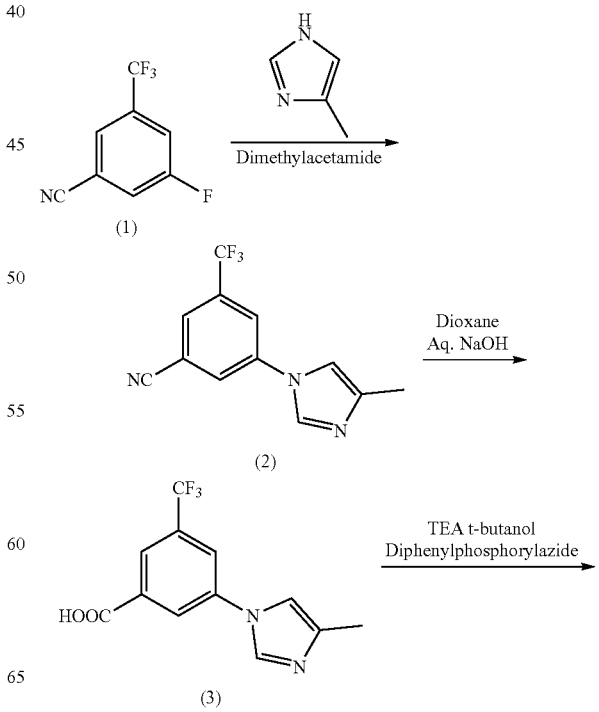

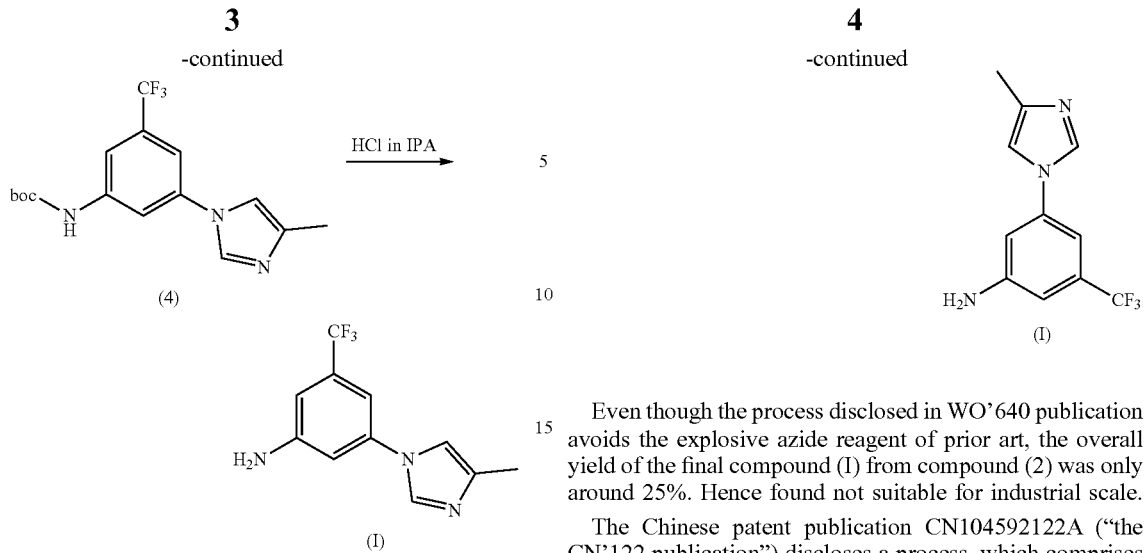

The disclosed process of WO'281 publication involves the use of toxic and a potential explosive azide such as diphenylphosphoryl azide for conversion of compound (3) to compound (4); further obtained carbamate intermediate (4) requires expensive and time consuming chromatographic purification. Hence this process is not suitable for industrial scale.

The PCT publication WO2006135640 ("the WO'640 publication") discloses alternative process for the preparation of compound of Formula (I), which is schematically represented by the following scheme:

Even though the process disclosed in WO'640 publication avoids the explosive azide reagent of prior art, the overall yield of the final compound (I) from compound (2) was only around 25%. Hence found not suitable for industrial scale.

The Chinese patent publication CN104592122A ("the CN'122 publication") discloses a process, which comprises coupling of 3-bromo-5-trifluoromethylbenzoic acid with 4-methyl-1H-imidazole, followed by hydrazinolysis, diazotization reaction, and Curtius rearrangement reaction to provide compound of Formula (I). The disclosed process was schematically represented by the following scheme:

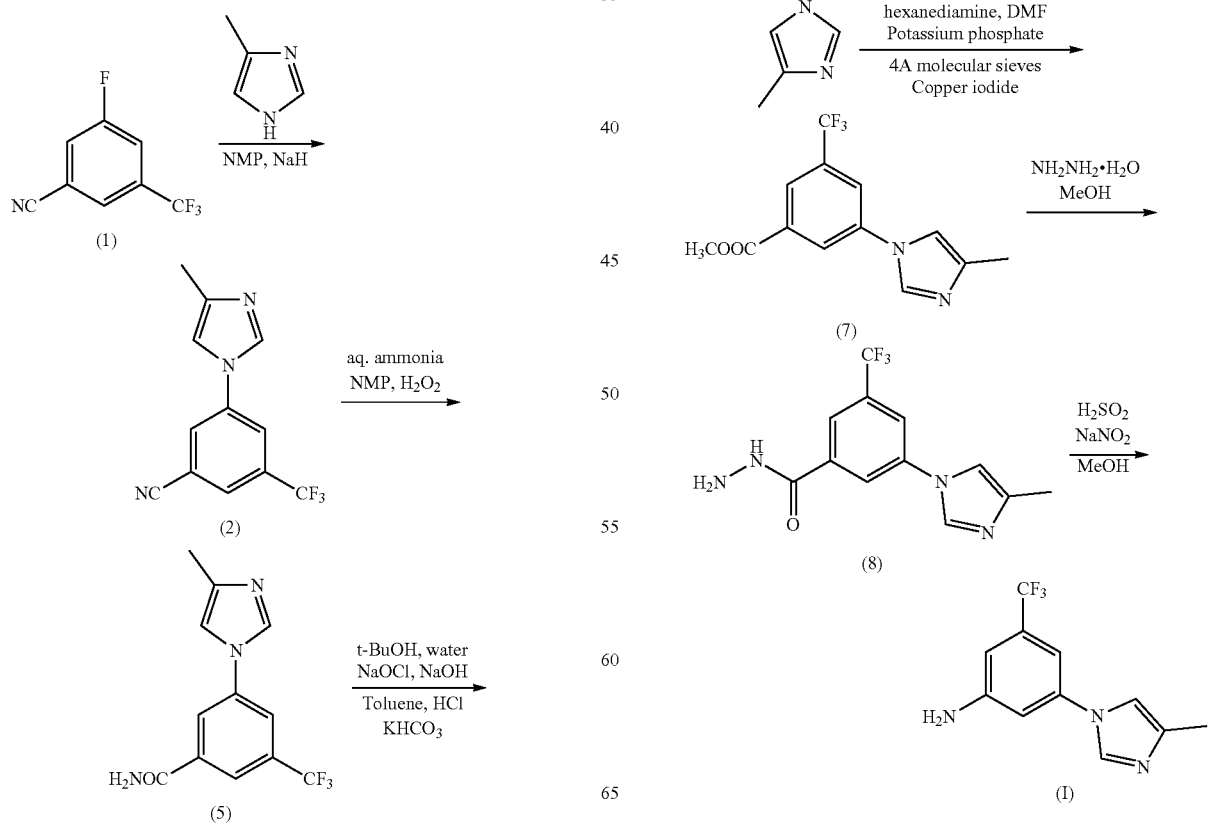

The European patent publication EP3095782A1 ("the EP'782 publication") discloses a preparation of 3-(4-methyl-1H-imidazol-1-yl)-5-(trifluoromethyl) aniline of Formula (I) via N-hydroxy-3-(4-methyl-imidazol-1-yl)-5-trifluoromethyl benzamide and the disclosed process schematically represented by the following scheme.

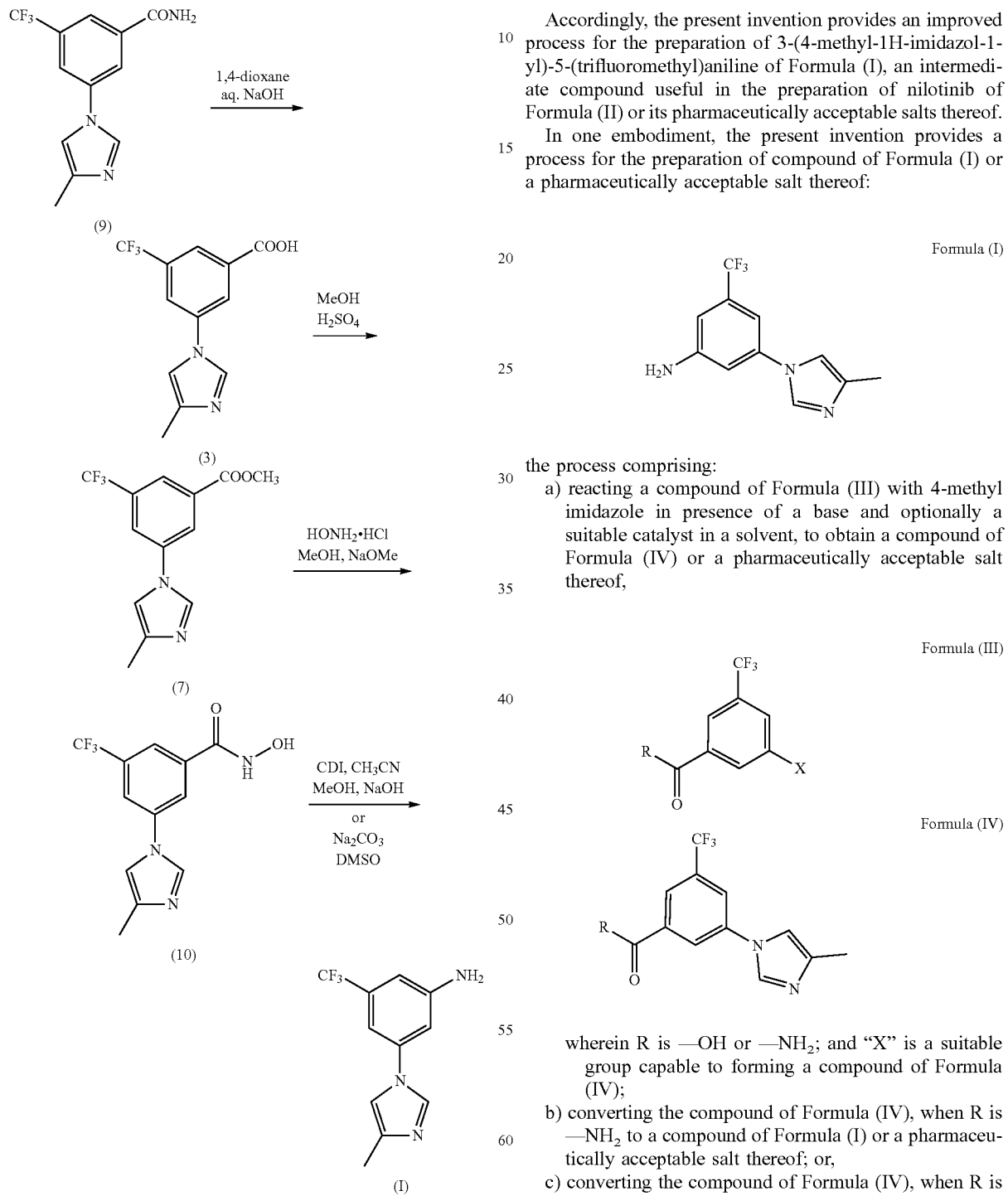

Even through the process disclosed in EP'782 publication results in higher yields compared to WO'640 publication, it involves large number of steps for the conversion of amide group of compound (9) into amine group of compound (I) and found not suitable for commercial scale.

Hence there is a need in the art to provide an improved process for the preparation of compound of Formula (I) which avoids the aforementioned problems of prior art.

SUMMARY OF THE INVENTION

Accordingly, the present invention provides an improved process for the preparation of 3-(4-methyl-1H-imidazol-1-yl)-5-(trifluoromethyl)aniline of Formula (I), an intermediate compound useful in the preparation of nilotinib of Formula (II) or its pharmaceutically acceptable salts thereof.

In one embodiment, the present invention provides a process for the preparation of compound of Formula (I) or a pharmaceutically acceptable salt thereof:

the process comprising:
a) reacting a compound of Formula (III) with 4-methyl imidazole in presence of a base and optionally a suitable catalyst in a solvent, to obtain a compound of Formula (IV) or a pharmaceutically acceptable salt thereof, wherein R is —OH or —NH$_2$; and "X" is a suitable group capable to forming a compound of Formula (IV);
b) converting the compound of Formula (IV), when R is —NH$_2$ to a compound of Formula (I) or a pharmaceutically acceptable salt thereof; or,
c) converting the compound of Formula (IV), when R is —OH to a compound of Formula (IV), wherein R is —NH$_2$, and converting the resulted compound of Formula (IV), wherein R is —NH$_2$ to a compound of Formula (I) or a pharmaceutically acceptable salt thereof.

In another embodiment, the present invention provides a process for the preparation of compound of Formula (I) or a pharmaceutically acceptable salt thereof, the process comprising:
  a) reacting a compound of Formula (III) with 4-methyl imidazole in presence of a base and optionally a suitable catalyst in a solvent to obtain a compound of Formula (IV) or a pharmaceutically acceptable salt thereof, wherein R is —OH or —NH$_2$; and "X" is selected from the group consisting of halides such as chloride, bromide, iodide and fluoride; sulfonates such as tosylate, mesylate, nosylate, triflate and the like; boronates such as boronic acid, boronic acid pinacol ester and the like;
  b) converting the compound of Formula (IV), when R is —NH$_2$ to a compound of Formula (I) or a pharmaceutically acceptable salt thereof; or,
  c) converting the compound of Formula (IV), when R is —OH to a compound of Formula (IV), wherein R is —NH$_2$, and converting the resulted compound of Formula (IV), wherein R is —NH$_2$ to a compound of Formula (I) or a pharmaceutically acceptable salt thereof.

In another embodiment, the present invention provides a process for the preparation of compound of Formula (I) or a pharmaceutically acceptable salt thereof: the process comprising:
  a) reacting an amide compound of Formula (III'),

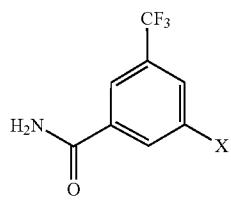

Formula (III')

wherein "X" is selected from the group consisting of halides such as chloride, bromide, iodide and fluoride; sulfonates such as tosylate, mesylate, nosylate, triflate and the like; boronates such as boronic acid, boronic acid pinacol ester and the like; with 4-methyl imidazole in presence of a base and optionally a suitable catalyst in a solvent to obtain a compound of Formula (IV'), and

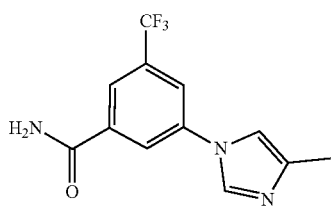

Formula (IV')

b) converting the compound of Formula (IV') to compound of Formula (I) or a pharmaceutically acceptable salt thereof.

In another embodiment, the present invention provides a process for the preparation of compound of Formula (I) or a pharmaceutically acceptable salt thereof: the process comprising:

a) hydrolysing a nitrile compound of Formula (V)

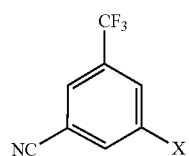

Formula (V)

wherein "X" is selected from the group consisting of halides such as chloride, bromide, iodide and fluoride; sulfonates such as tosylate, mesylate, nosylate, triflate and the like; boronates such as boronic acid, boronic acid pinacol ester and the like; with an acid, or with peroxide reagent in presence of a suitable base to obtain an amide compound of Formula (III'),

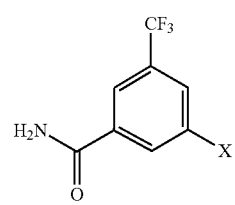

Formula (III')

b) reacting the amide compound of Formula (III'), wherein "X" is defined as above; with 4-methyl imidazole in presence of a base and optionally a suitable catalyst in a solvent to obtain a compound of Formula (IV'), and

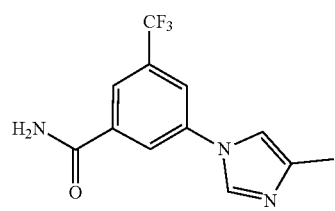

Formula (IV')

c) converting the compound of Formula (IV') to compound of Formula (I) or a pharmaceutically acceptable salt thereof.

In another embodiment, the present invention provides a process for the preparation of compound of Formula (I) or a pharmaceutically acceptable salt thereof, the process comprising:
  i) reacting an acid compound of formula (III")

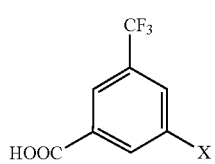

Formula (III")

wherein "X" is selected from the group consisting of halides such as chloride, bromide, iodide and fluoride; sulfonates such as tosylate, mesylate, nosylate, triflate and the like; boronates such as boronic acid, boronic acid pinacol ester and the like; with 4-methyl imidazole in presence of a base and optionally a suitable catalyst in a solvent to obtain an acid compound of Formula (IV"),

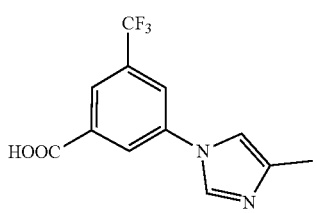

Formula (IV")

ii) converting the acid compound of formula (IV") to a compound of Formula (IV'), and

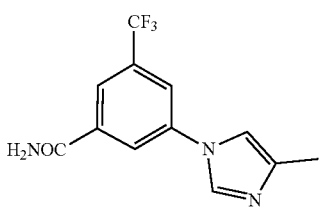

Formula (IV')

iii) converting the compound of Formula (IV') to compound of Formula (I).

In another embodiment, the present invention provides a process for the preparation of compound of Formula (I) or a pharmaceutically acceptable salt thereof: the process comprising:

i) hydrolysing a nitrile compound of Formula (V)

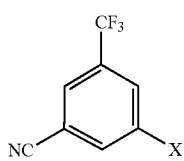

Formula (V)

wherein "X" is selected from the group consisting of halides such as chloride, bromide, iodide and fluoride; sulfonates such as tosylate, mesylate, nosylate, triflate and the like; boronates such as boronic acid, boronic acid pinacol ester and the like; with a suitable acid or a base to obtain an acid compound of Formula (III").

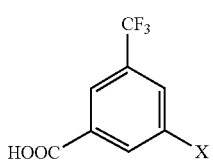

Formula (III")

wherein "X" is defined as above, ii) reacting the acid compound of Formula (III") with 4-methyl imidazole in presence of a base and optionally a suitable catalyst in a solvent to obtain an acid compound of Formula (IV"),

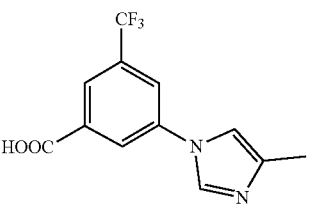

Formula (IV")

iii) converting the acid compound of Formula (IV") to a compound of Formula (IV'), and

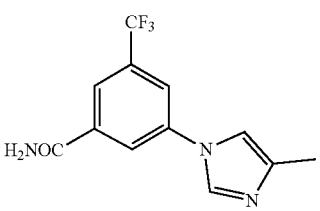

Formula (IV')

iv) converting the compound of Formula (IV') to compound of Formula (I).

In another embodiment, the present invention provides crystalline form of 3-fluoro-5-(trifluoromethyl)-benzamide, which is characterized by a powder X-Ray diffraction pattern having one or more peaks at about 5.8, 11.65, 16.35, 17.5, 18.3, 18.6, 20, 20.7, 21.35, 21.8, 23.9, 24.40, 25.30, 26.15, 26.4, 27.75, 28.6, 29.4, 29.90, 33.71, 35 and 35.4±0.2° 2θ; herein after designated as crystalline Form L1.

In another embodiment, the present invention provides crystalline Form L1 of 3-fluoro-5-(trifluoromethyl)-benzamide characterized by PXRD pattern substantially as shown in the FIGURE.

In another embodiment, the present invention provides a process for the preparation of crystalline Form L1 of 3-fluoro-5-(trifluoromethyl)benzamide, which process comprising: hydrolysing 3-fluoro-5-(trifluoromethyl) benzonitrile with peroxide reagent and a suitable base in dimethyl sulfoxide, water or mixtures thereof.

In another embodiment, the present invention provides a process for the preparation of crystalline Form L1 of 3-fluoro-5-(trifluoromethyl)benzamide, which process comprising: hydrolysing 3-fluoro-5-(trifluoromethyl) benzonitrile with hydrogen peroxide and potassium carbonate in dimethyl sulfoxide, water or mixtures thereof.

In another embodiment, the present invention provides a process for the preparation of crystalline Form L1 of 3-fluoro-5-(trifluoromethyl)benzamide, which process comprising: crystallizing 3-fluoro-5-(trifluoromethyl)benzamide in dimethyl sulfoxide, water or mixtures thereof.

In another embodiment, the present invention provides a process for the preparation of nilotinib of Formula (II) or pharmaceutically acceptable salts thereof, which comprises: preparing a compound of Formula (I) according to processes described as above and converting the compound of Formula (I) to nilotinib or pharmaceutically acceptable salts thereof.

In another embodiment, the present invention provides pharmaceutical composition comprising nilotinib or pharmaceutically acceptable salts thereof prepared according to the processes as described above.

BRIEF DESCRIPTION OF THE DRAWINGS

The accompanying drawings, which are incorporated in and constitute a part of this specification, illustrate several embodiments of the invention and together with the description, serve to explain the principles of the invention.

The FIGURE shows the characteristic powder X-ray diffraction (XRD) pattern of 3-fluoro-5-(trifluoromethyl) benzamide.

DETAILED DESCRIPTION OF THE INVENTION

The present invention provides a process for the preparation of 3-(4-methyl-1H-imidazol-1-yl)-5-(trifluoromethyl) aniline of Formula (I), an intermediate compound useful in the preparation of nilotinib of Formula (II) or its pharmaceutically acceptable salts thereof, which is having least number of steps and easy to scale in commercial scale.

In one embodiment, the present invention provides a process for the preparation of compound of Formula (I) or a pharmaceutically acceptable salt thereof:

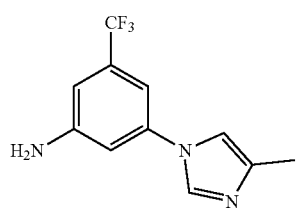

Formula (I)

the process comprising:
a) reacting a compound of Formula (III) with 4-methyl imidazole in presence of a base and optionally a suitable catalyst in a solvent to obtain a compound of Formula (IV) or a pharmaceutically acceptable salt thereof,

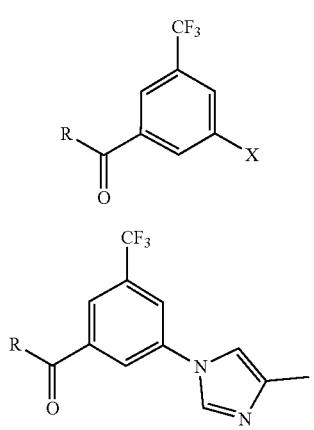

Formula (III)

Formula (IV)

wherein R is —OH or —NH$_2$; and "X" is a suitable group capable to forming a compound of Formula (IV);
b) converting the compound of Formula (IV), when R is —NH$_2$ to a compound of Formula (I) or a pharmaceutically acceptable salt thereof; or,
c) converting the compound of Formula (IV), when R is —OH to a compound of Formula (IV), wherein R is —NH$_2$, and converting the resulted compound of Formula (IV), wherein R is —NH$_2$ to a compound of Formula (I) or a pharmaceutically acceptable salt thereof.

The starting compound of Formula (III), wherein R is —OH or —NH$_2$ can be prepared by the process described as per below embodiments.

The step a) of forgoing process involves reaction of compound of Formula (III), wherein R is —OH or —NH$_2$; and "X" is selected from the group consisting of halides such as chloride, bromide, iodide and fluoride; sulfonates such as tosylate, mesylate, nosylate, triflate and the like; boronates such as boronic acid, boronic acid pinacol ester and the like; preferably halides and more preferably fluoride; with 4-methyl imidazole in presence of a base and optionally a suitable catalyst in a solvent to obtain a compound of Formula (IV) or a pharmaceutically acceptable salt thereof.

The suitable base used herein step a) is selected from either inorganic base or organic base; further, the suitable inorganic base is selected from, but is not limited to, alkali metal hydroxides such as sodium hydroxide, potassium hydroxide and the like; alkali metal hydrides such as sodium hydride, potassium hydride and the like; alkali metal amides such as sodium amide, potassium amide, lithium amide and the like; alkali metal alkoxides such as sodium methoxide, sodium ethoxide, sodium t-butoxide, potassium t-butoxide and the like; alkali metal carbonates such as sodium carbonate, potassium carbonate, cesium carbonate and the like; alkali metal bicarbonates such as sodium bicarbonate, potassium bicarbonate and the like; phosphates such as sodium phosphate, trisodium phosphate, potassium phosphate, tripotassium phosphate and the like; ammonium carbonate; and the organic base is selected from, but is not limited to, triethylamine, tri-n-propylamine, tri-n-butylamine, methyldibutylamine, diisopropylamine, dicyclohexylamine, methyl dicyclohexylamine, ethyldiisopropyl amine, N,N-diethyl dicyclohexylamine, pyridine, dimethylamino-4-pyridine, N-methyl piperidine, N-ethylpiperidine, N-ethylpiperidine, N-butylpiperidine, 1,2-dimethyl piperidine and the like; or mixtures thereof. Preferably the base used herein is selected from sodium hydroxide, potassium hydroxide, sodium hydride, sodium amide, potassium t-butoxide, sodium carbonate, potassium carbonate, trisodium phosphate, sodium bicarbonate, triethylamine, diisopropylamine and mixtures thereof; more preferably sodium hydroxide, potassium hydroxide, sodium amide, tripotassium phosphate and mixtures thereof.

The suitable catalyst, which is optionally used herein in step a) is selected from either copper salt in presence of an additive, or a palladium catalyst optionally in presence of an additional ligand; copper salt used herein is selected from, but is not limited to, cuprous bromide, cupric bromide, cuprous iodide, cuprous chloride, cupric chloride, cuprous nitrate, cuprous sulphate and the like; and the additives used herein is selected from glucosamine, ethylenediamine, cyclohexyldiamine, ethyleneglycol, 8-hydroxy quinolone, proline, sacrosine, N-methyl sacropsine and the like. The palladium catalyst used herein is selected from, but is not limited to, Tris(dibenzylideneacetone)dipalladium(0) [Pd$_2$ (dba)₃], 1,1'-Bis(diphenylphosphino) ferrocene-palladium (II)dichloride dichloromethane complex [Pd(dppf) Cl₂.DCM], palladium diacetate and the like; the ligand used herein is selected from Bis[(2-diphenylphosphino)phenyl] ether [DPEPhos], 4,5-Bis(diphenylphosphino)-9,9-dimethylxanthene [Xantphos] and the like. Preferably the catalyst used herein is selected from 1,1'-Bis(diphenylphosphino) ferrocene-palladium(II)dichloride dichloromethane complex, a combination of palladium diacetate and Bis[(2-diphenylphosphino)phenyl] ether, or a combination of 1,1'-Bis(diphenylphosphino) ferrocene-palladium(II)dichloride dichloromethane complex and Bis[(2-diphenyl phosphino) phenyl] ether.

The suitable solvent used herein in step a) is selected from, but is not limited to ketones such as acetone, methyl ethyl ketone, methyl isobutyl ketone, diethyl ketone and the like; nitriles such as acetonitrile, propionitrile and the like; ethers such as diethyl ether, tetrahydrofuran, methyl tetrahydrofuran, 1,4-dioxane and the like; esters such as ethyl acetate, propyl acetate, isopropyl acetate, butyl acetate and the like; polar aprotic solvent such as dimethylacetamide, dimethylformamide, dimethylsulfoxide, N-methylpyrrolidone and the like; water or mixtures thereof; preferably polar aprotic solvent and more preferably dimethylacetamide.

The step a) reaction may advantageously be carried out at a suitable temperature of about 20° C. to about reflux temperature of the solvent, preferably at about 75° C. to about 150° C. for a sufficient period of time from about 30 min to until completion of the reaction, preferably for about 3 to 12 hrs.

The step b) of the forgoing process involves converting the compound of Formula (IV), when R is —NH₂ to a compound of Formula (I) or a pharmaceutically acceptable salt thereof. The conversion of compound of Formula (IV), wherein R is —NH₂ to a compound of Formula (I) can be carried out under Hofmann reaction conditions i.e., reacting the compound of Formula (IV), where R is —NH₂ with halogen in presence of an alkali metal base or alkali metal hypohalite to provide compound of Formula (I). The halogen used herein, for example chlorine or bromine; whereas the alkali metal hypohalite can be sodium hypochlorite or sodium hypobromite; The alkali metal compounds used herein, for example selected from sodium hydroxide, potassium hydroxide, sodium carbonate, potassium carbonate and the like; preferably Hoffmann reaction of compound of formula (IV) is carried out with bromine in presence of aqueous sodium hydroxide.

The step b) reaction may advantageously be carried out at a suitable temperature of about 20° C. to about reflux temperature, preferably at about 85-95° C. for a sufficient period of time from about 30 min to until completion of the reaction, preferably for 2-5 hrs.

The step c) of the forgoing process involves converting the compound of Formula (IV), when R is —OH to a compound of Formula (IV), wherein R is —NH₂, and converting the resulted compound of Formula (IV), wherein R is —NH₂ to a compound of Formula (I) or a pharmaceutically acceptable salt thereof.

The conversion of the compound of Formula (IV), wherein R is —OH to a compound of Formula (IV), wherein R is —NH₂ can be carried out by treating the compound of Formula (IV), wherein R is —OH with suitable amine source in presence of a suitable activating agent and a suitable solvent. The suitable activating agent used herein is selected from thionyl chloride, thionylbromide, oxalylchloride, oxalylbromide, phosphorous trichloride, phosphorous tribromide and phosphorous pentachloride. The suitable amine source is selected from ammonia, ammonium hydroxide and the like. The suitable solvent used herein is selected from the group consisting of nitriles such as acetonitrile, propionitrile and the like, alcohols such as methanol, ethanol, isopropanol and the like; hydrocarbons like toluene, heptane, hexane and the like; chloro solvent such as methylene chloride, chloroform and the like; or mixtures thereof; where as the conversion of compound of Formula (IV), wherein R is —NH₂ to a compound of Formula (I) or a pharmaceutically acceptable salt thereof, can be carried out as described above in step b).

The compound of Formula (I) recovered using the process of the invention can be isolated as its free base or its suitable acid addition salt thereof. The step of forming acid addition salt of compound of Formula (I) is not only for isolation of compound of Formula (I) but is advantageously removes impurities formed if any during the process of the invention.

The step of forming acid addition salt of compound of Formula (I) is carried out by treating the compound of Formula (I) with a suitable acid in a solvent; wherein the suitable acid is either inorganic acid or organic acid; further inorganic acid is selected from but not limited to hydrochloric acid, hydrobromic acid, sulphuric acid, phosphoric acid and the like; and organic acid is selected from but not limited to, methane sulfonic acid, ethane sulfonic acid, benzene sulfonic acid and p-toluene sulfonic acid, acetic acid, formic acid, oxalic acid, citric acid, malic acid, maleic acid and the like; preferably hydrochloric acid.

The free base compound of Formula (I) can be liberated by treating the acid addition salt of compound of Formula (I) with a suitable base in a solvent. The suitable base used herein is selected from, but not limited to, alkali metal hydroxides such as sodium hydroxide, potassium hydroxide, lithium hydroxide and the like; alkali metal carbonates such as sodium carbonate, potassium carbonate, cesium carbonate and the like; alkali metal bicarbonates such as sodium bicarbonate, potassium bicarbonate and the like; preferably sodium bicarbonate.

The solvent used herein for saltification and basification are selected from, but not limited to, alcohols, such as methanol, ethanol, isopropanol, butanol and the like; ketones such as acetone, methyl ethyl ketone, methyl isobutyl ketone, diethyl ketone and the like; nitriles such as acetonitrile, propionitrile and the like; esters such as ethyl acetate, propyl acetate, isopropyl acetate, butyl acetate and the like; water or mixtures thereof; preferably water or acetone.

In another embodiment, the present invention provides a process for preparation of a compound of Formula (III)

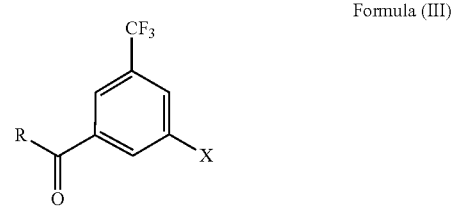

Formula (III)

wherein R is —OH or —NH₂; and "X" is defined as above, from a nitrile compound of Formula (V).

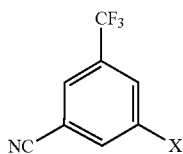

Formula (V)

In another embodiment, the compound of Formula (III), wherein R is —NH$_2$ is prepared by hydrolysing a nitrile compound of Formula (V)

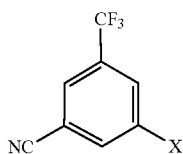

Formula (V)

wherein "X" is selected from the group consisting of halides such as chloride, bromide, iodide and fluoride; sulfonates such as tosylate, mesylate, nosylate, triflate and the like; boronates such as boronic acid, boronic acid pinacol ester and the like; preferably X is halide and more preferably fluoride; with a suitable acid or with peroxide reagent in presence of a suitable base in presence or absence of a solvent to obtain an amide compound of Formula (III), wherein R is —NH$_2$.

The suitable acid used herein is selected from hydrochloric acid, hydrobromic acid, sulphuric acid, acetic acid, formic acid, trifluoroacetic acid, methanesulfonic acid and mixtures thereof; preferably mixture of acids and more preferably mixture of methane sulfonic acid and sulphuric acid.

The suitable peroxide reagent used herein is selected from hydrogen peroxide, urea-hydrogen peroxide and the like; preferably hydrogen peroxide; and the base is selected from the group consisting of, but is not limited to alkali metal hydroxides such as sodium hydroxide, potassium hydroxide, lithium hydroxide and the like; alkali metal carbonates such as sodium carbonate, potassium carbonate, cesium carbonate and the like; alkali metal bicarbonates such as sodium bicarbonate, potassium bicarbonate and the like; preferably alkali metal carbonates and more preferably potassium carbonate.

The solvent used herein is selected from, but not limited to, alcohols such as methanol, ethanol, isopropanol, butanol, t-butanol and the like; ketones such as acetone, methyl ethyl ketone, methyl isobutyl ketone, diethyl ketone and the like; sulfoxides such as dimethylsulfoxide; ethers such as diethyl ether, tetrahydrofuran, methyl tetrahydrofuran and the like; water or mixtures thereof; preferably dimethylsulfoxide. The hydrolysis reaction may suitably be carried out at a temperature of about 10° C. to about 80° C., preferably at about 25-75° C. for sufficient period of time to complete the reaction, preferably for about 30 mins to 4 hrs.

In another embodiment, the compound of Formula (III), wherein R is —OH is prepared by hydrolysing a nitrile compound of Formula (V)

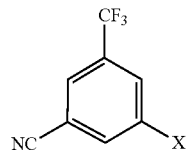

Formula (V)

wherein "X" is selected from the group consisting of halides such as chloride, bromide, iodide and fluoride; sulfonates such as tosylate, mesylate, nosylate, triflate and the like; boronates such as boronic acid, boronic acid pinacol ester and the like; preferably X is halide and more preferably fluoride; with a suitable acid or a base in a solvent to obtain an acid compound of Formula (III), wherein R is —OH.

The suitable acid used herein for the preparation of acid compound of Formula (III), wherein R is —OH, selected from but not limited to hydrochloric acid, hydrobromic acid, sulphuric acid, phosphoric acid, nitric acid and the like; and a suitable base used herein selected from but not limited to hydroxides such as sodium hydroxide, potassium hydroxide, magnesium hydroxide, calcium hydroxide and the like; alkoxides of alkali metals such as sodium methoxide, sodium ethoxide, sodium t-butoxide, potassium t-butoxide and the like; carbonate such as sodium carbonate, potassium carbonate and the like. Preferably hydrolysis reaction of Formula (V) is carried out in presence of a hydroxide base and more preferably sodium hydroxide.

The solvent used herein is selected from polar aprotic solvent such as dimethylacetamide, dimethylformamide, dimethylsulfoxide, 1,4-dioxane and the like; alcohols such as methanol, ethanol, butanol and the like; nitriles such as acetonitrile, propionitrile and the like; water, or mixtures thereof; preferably water.

The hydrolysis reaction compound of Formula (V) to provide compound of Formula (III), wherein R is —OH, may suitably be carried out at a temperature of about 20° C. to about reflux temperature, preferably at about 80-100° C. for a sufficient period of time to complete the reaction, preferably for 1 to 4 hrs.

In another embodiment, the present invention provides crystalline form of 3-fluoro-5-(trifluoromethyl)benzamide which is characterized by a powder X-Ray diffraction pattern having one or more peaks at about 5.8, 11.65, 16.35, 17.5, 18.3, 18.6, 20, 20.7, 21.35, 21.8, 23.9, 24.40, 25.30, 26.15, 26.4, 27.75, 28.6, 29.4, 29.90, 33.71, 35 and 35.4±0.2° 2θ; herein after designated as crystalline Form L1.

In another embodiment, the present invention provides crystalline Form L1 of 3-fluoro-5-(trifluoromethyl)-benzamide characterized by PXRD pattern shown in the FIGURE.

In another embodiment, the present invention provides a process for the preparation of crystalline Form L1 of 3-fluoro-5-(trifluoromethyl)benzamide, which process comprising: hydrolyzing 3-fluoro-5-(trifluoromethyl) benzonitrile with peroxide reagent and a suitable base in dimethyl sulfoxide, water or mixtures thereof.

The suitable peroxide reagent used herein is selected from hydrogen peroxide, urea-hydrogen peroxide and the like; preferably hydrogen peroxide, and a suitable base used herein is selected from the group consisting of, but is not limited to alkali metal hydroxides such as sodium hydroxide, potassium hydroxide, lithium hydroxide and the like; alkali metal carbonates such as sodium carbonate, potassium carbonate, cesium carbonate and the like; alkali metal bicarbonates such as sodium bicarbonate, potassium bicarbonate and the like; preferably potassium carbonate.

The hydrolysis of 3-fluoro-5-(trifluoromethyl) benzonitrile is suitably carried out at a temperature of about 10° C. to about 40° C. for sufficient period of time, for example 1-2 hrs. Then the isolation of crystalline Form L1 of 3-fluoro-5-(trifluoromethyl)benzamide from the reaction mass can be carried out by any conventional techniques known in the art, for example, adding water to the reaction mass, stirring, filtration and followed by drying.

In another embodiment, the present invention provides a process for the preparation of crystalline Form L1 of 3-fluoro-5-(trifluoromethyl)benzamide, which process comprising: mixing 3-fluoro-5-(trifluoromethyl)benzamide in dimethyl sulfoxide, water or mixture thereof and isolating the crystalline Form L1.

The X-Ray powder diffraction can be measured using PANalytical X'per³pro X-ray powder diffractometer equipped with a Cu-anode ($[\lambda]=1.54$ Angstrom), X-ray source operated at 45 kV, 40 mA. Two-theta calibration is performed using an NIST SRM 640c Si standard. The sample was analysed using the following instrument parameters: measuring range=3-45°2θ; step size=0.01°; and Time per step=15 sec.

EXAMPLES

The following examples are provided by way of illustration only, and are not intended to be limiting of the present invention.

Example-1: Preparation of 3-fluoro-5-(trifluoromethyl) benzamide

In 2 lit three necked round bottom flask equipped with mechanical stirrer, thermometer and an addition funnel, 3-fluoro-5(trifluoromethyl)benzonitrile (100 g) and dimethylsulfoxide (200 ml) was added at 25-35° C. and stirred for 20 min. To this, potassium carbonate (220 g) and hydrogen peroxide solution (140 ml) were added at 25-35° C. and stirred for 90 mins. After completion of reaction, water (1200 ml) was added to the reaction mass and stirred for an hour. Filtered the solid, washed with water, suck dried and then dried at 50-55° C. under vacuum for 6 hrs to get the title compound. Yield: 103 g.

Example-2: Preparation of 3-fluoro-5-(trifluoromethyl) benzamide

In 4 lit three necked round bottom flask equipped with mechanical stirrer, thermometer and an addition funnel, 3-fluoro-5(trifluoromethyl)benzonitrile (100 g), methanesulfonic acid (148 g) and sulfuric acid (50 ml) was added, heated to 70-75° C. and stirred for 3 hrs at the same temperature. After completion of reaction, the reaction mass was cooled to 25-35° C. and quenched into water (2000 ml) over a period of 60 min. The precipitated material was stirred for 30 min, filtered and the solid washed with water. Then wet solid was dried at 55-60° C. under vacuum for 8 hrs to get the title compound. Yield: 104 g; HPLC purity: 99.7%

Example-3: Preparation of 3-fluoro-5-(trifluoromethyl) benzamide

In 1 lit three necked round bottom flask equipped with mechanical stirrer, thermometer and an addition funnel, 3-fluoro-5(trifluoromethyl)benzonitrile (10 g), trifluoroacetic acid (20 ml) and sulfuric acid (5 ml) was added, heated to 70-75° C. and stirred for 3 hrs at the same temperature. After completion of reaction, the reaction mass was cooled to 25-35° C. and quenched into cold water (200 ml) over a period of 60 min. The precipitated material was stirred for 30 min, filtered and the solid was washed with water. Then wet solid was dried at 55-60° C. under vacuum for 8 hrs to get the title compound. Yield: 10.3 g; HPLC purity: 99.6%

Example-4: Preparation of 3-fluoro-5-(trifluoromethyl) benzamide

In 1 lit three necked round bottom flask equipped with mechanical stirrer, thermometer and an addition funnel, 3-fluoro-5(trifluoromethyl)benzonitrile (5 g), acetic acid (20 ml) and sulfuric acid (5 ml) was added, heated to 80-85° C. and stirred for 4 hrs at the same temperature. After completion of reaction, the reaction mass was cooled to 25-35° C. and quenched into cold water (100 ml) over a period of 60 min. The precipitated material was stirred for 30 min, filtered and the solid was washed with water. Then wet solid was dried at 55-60° C. under vacuum for 8 hrs to get the title compound. Yield: 4.5 g.

Example-5: Preparation of 3-(4-methyl-1H-imidazol-1-yl)-5-(trifluoromethyl) benzamide In 5 lit four necked round bottom flask equipped with mechanical stirrer, thermometer, reflux condenser and an addition funnel, dimethylacetamide (500 ml) and 4-methylimidazole (60 g) was taken and stirred for 15 mins at 25-35° C. To this, sodium amide (30.2 g) was added and stirred for 45 mins at 25-35° C. 3-fluoro-5-(trifluoromethyl) benzamide (100 g) was added to the above reaction mass at 25-35° C. Then the reaction mass was heated to 80-85° C. and stirred for 12 hrs at the same temperature. After completion of reaction, the reaction mass was cooled to room temperature, water (2500 ml) was added to it and stirred for 3 hrs. The precipitated solid was filtered, washed with water and dried at 60-70° C. under vacuum for 12 hrs to get the title compound. Yield: 100 g.

Example-6: Preparation of 3-(4-methyl-1H-imidazol-1-yl)-5-(trifluoromethyl) benzamide In 3 lit four necked round bottom flask equipped with mechanical stirrer, thermometer, reflux condenser and an addition funnel, 4-methylimidazole (25 g), potassium hydroxide (27.1 g), dimethylacetamide (250 ml), 3-fluoro-5-(trifluoromethyl) benzamide (50 g) were added and the reaction mass was heated to 140-145° C. and stirred for 4 hrs at the same temperature. After completion of reaction, the reaction mass was cooled to room temperature, water (1250 mL) was added to it and stirred for 2 hrs at room temperature. The precipitated solid was filtered, washed with water and dried under vacuum at 55-60° C. for 8 hrs to get the title compound. Yield: 50 g.

Example-7: Preparation of 3-(4-methyl-1H-imidazol-1-yl)-5-(trifluoromethyl) benzamide In 3 lit four necked round bottom flask equipped with mechanical stirrer, thermometer, reflux condenser and an addition funnel, 4-methylimidazole (5 g), sodium hydroxide (7.7 g), dimethylacetamide (70 ml), 3-fluoro-5-(trifluoromethyl) benzamide (10 g) were added and the reaction mass was heated to 140-145° C. and stirred for 4 hrs at the same temperature. After completion of reaction, the reaction mass was cooled to room temperature, water (1250 mL) was added to it and stirred for 2 hrs at room temperature. The precipitated solid was filtered, washed with water and dried under vacuum at 55-60° C. for 8 hrs to get the title compound. Yield: 8 g.

Example-8: Preparation of 3-(4-methyl-1H-imidazol-1-yl)-5-(trifluoromethyl) benzamide In 3 lit four necked round bottom flask equipped with mechanical stirrer, thermometer, reflux condenser and an addition funnel, 3-fluoro-5-(trifluoromethyl)benzamide (10 g) and dimethylacetamide (50 ml), was added under nitrogen atmosphere and stirred. To this solution, tripotassium phosphate (20.5 g), 4-methyl imidazole (4.76 g), Tris(dibenzylideneacetone)dipalladium(0) (0.44 g) and Bis[(2-diphenylphosphino) phenyl] ether (0.26 g) were added. The reaction mass was heated to 120-130° C. and stirred for 4 hrs at the same temperature. After completion of reaction, the mixture was cooled to room temperature; water (200 mL) was added to it and stirred for 2 hrs at room temperature. The precipitated solid was filtered, washed with water and dried under vacuum at 55-60° C. for 8 hrs to get the title compound.
Yield: 10.5 g

Example-9: Preparation of 3-(4-methyl-1H-imidazol-1-yl)-5-(trifluoromethyl) benzamide In 3 lit four necked round bottom flask equipped with mechanical stirrer, thermometer, reflux condenser and an addition funnel, 3-fluoro-5-(trifluoromethyl)benzamide (10 g) and dimethylacetamide (50 ml), was added under nitrogen atmosphere and stirred. To this solution, tripotassium phosphate (20.5 g), 4-methyl imidazole (4.76 g), 1,1'-Bis(diphenylphosphino)ferrocene-palladium(II)dichloride dichloromethane complex (0.4 g) were added. The reaction mass was heated to 120-130° C. and stirred for 4 hrs at the same temperature. After completion of reaction, the mixture was cooled to room temperature; water (200 mL) was added to it and stirred for 2 hrs at room temperature. The precipitated solid was filtered, washed with water and dried under vacuum at 55-60° C. for 8 hrs to get the title compound. Yield: 7.5 g.

Example-10: Preparation of 3-(4-methyl-1H-imidazol-1-yl)-5-(trifluoromethyl) benzamide In 3 lit four necked round bottom flask equipped with mechanical stirrer, thermometer, reflux condenser and an addition funnel, 3-fluoro-5-(trifluoromethyl)benzamide (10 g) and dimethylacetamide (40 ml), was added under nitrogen atmosphere and stirred. To this solution, tripotassium phosphate (20.5 g), 4-methyl imidazole (4.76 g), palladium diacetate (100 mg) and Bis[(2-diphenylphosphino)phenyl] ether (150 mg) were added. The reaction mass was heated to 120-130° C. and stirred for 10 hrs at the same temperature. After completion of reaction, the mixture was cooled to room temperature; water (200 mL) was added to it and stirred for 2 hrs at room temperature. The precipitated solid was filtered, washed with water and dried under vacuum at 55-60° C. for 8 hrs to get the title compound. Yield: 11.2 g.

Example-11: Preparation of 3-(4-methyl-1H-imidazol-1-yl)-5-(trifluoromethyl) benzamide In 3 lit four necked round bottom flask equipped with mechanical stirrer, thermometer, reflux condenser and an addition funnel, 3-fluoro-5-(trifluoromethyl)benzamide (10 g) and dimethylacetamide (40 ml), was added under nitrogen atmosphere and stirred. To this solution, potassium hydroxide (5.42 g), 4-methyl imidazole (5 g), palladium diacetate (100 mg) and Bis[(2-diphenylphosphino)phenyl] ether (150 mg) were added. The reaction mass was heated to 120-130° C. and stirred for 10 hrs at the same temperature. After completion of reaction, the mixture was cooled to room temperature; water (250 mL) was added to it and stirred for 2 hrs at room temperature. The precipitated solid was filtered, washed with water and dried under vacuum at 55-60° C. for 8 hrs to get the title compound. Yield: 10.5 g.

Example-12: Preparation of 3-(4-methyl-1H-imidazol-1-yl)-5-(trifluoromethyl) aniline hydrochloride In 2 lit three necked round bottom flask equipped with mechanical stirrer, thermometer and an addition funnel, sodium hydroxide (140 g) and water (1000 ml) were added at 25-35° C., stirred and cooled to 0-5° C. To this, bromine (21 ml) and 3-(4-methyl-1H-imidazol-1-yl)-5-(trifluoromethyl)benzamide (100 g) was added at 0-5° C. and stirred for 20 mins. The reaction mass was heated to 85-95° C. and stirred for 3 hrs at the same temperature. After completion of reaction, the reaction mass was allowed to cool to 25-35° C. and stirred for 3 hrs at the same temperature. The precipitated solid was filtered, washed with water and dried under vacuum at 60-70° C. for 6 hrs to get the title compound. Yield: 80 g.

Example 13: Preparation of 3-(4-methyl-1H-imidazol-1-yl)-5-(trifluoromethyl) aniline hydrochloride In 2 lit four necked round bottom flask equipped with mechanical stirrer, thermometer, reflux condenser and an addition funnel, 3-(4-methyl-1H-imidazol-1-yl)-5-(trifluoromethyl) aniline (80 g) and acetone (700 ml) was added at 25-35° C. and stirred for 10 mins at the same temperature. To this, concentrated hydrochloric acid (70 ml) was added at 25-35° C. The reaction mass was heated to 55-60° C. and stirred for an hour at reflux. The reaction mass was allowed to cool to 25-35° C. and stirred for an hour. The solid obtained was filtered, washed with acetone and dried under vacuum at 50° C. for 6 hrs to get the title compound. Yield: 65 g; HPLC purity: 99.5%; 5-regioisomer: 0.3%.

Example 14: Preparation of 3-(4-methyl-1H-imidazol-1-yl)-5-(trifluoromethyl) aniline In 2 lit three necked round bottom flask equipped with mechanical stirrer, thermometer and an addition funnel, water (600 ml) and 3-(4-methyl-1H-imidazol-1-yl)-5-(trifluoromethyl) aniline hydrochloride (100 g) was added and stirred at 25-35° C. Reaction mass was basified with 20% sodium carbonate solution at 25-35° C. and stirred for 3 hrs at the same temperature. The solid obtained was filtered, washed with water and dried under vacuum at 60-70° C. for 8 hrs to get the title compound. Yield: 75 g.

Example 15: Preparation of 3-(4-methyl-1H-imidazol-1-yl)-5-(trifluoromethyl) aniline In 3 lit three necked round bottom flask equipped with mechanical stirrer, thermometer and an addition funnel, methanol (500 ml) and 3-(4-methyl-1H-imidazol-1-yl)-5-(trifluoromethyl) aniline hydrochloride (100 g) was added and heated to reflux for complete dissolution. Sodium bicarbonate solution (105 g of sodium bicarbonate dissolved in 1500 ml water) was added to the reaction mass over a period of 60 min at reflux temperature. The reaction mass was cooled to room temperature and stirred for 3 hrs at the same temperature. The precipitated solid was filtered, washed with water and dried under vacuum at 60-70° C. for 8 hrs to get the title compound. Yield: 75 g; HPLC purity: 99.7%; 5-regioisomer: 0.03%.

Example-16: Preparation of 3-fluoro-5-(trifluoromethyl)benzoic acid

In 100 ml four necked round bottom flask equipped with mechanical stirrer, thermometer, reflux condenser and an addition funnel, sodium hydroxide (6.35 g) and water (10 ml) was added and stirred for 15 mins at 25-35° C. To this, 3-fluoro-5-(trifluoromethyl)benzonitrile (10 g) was added and heated to 85-90° C. The reaction mass was stirred at 85-90° C. for 2 hrs. After completion of reaction, the reaction mass was allowed to cool to 25-35° C. Then, the reaction mass was acidified with aqueous hydrochloric acid and stirred for 30 mins at 25-35° C. The solid formed was filtered, washed with water, suck dried and then dried under vacuum at 50-55° C. for 6 hrs to get the title compound. Yield: 8 g.

Example-17: Preparation of 3-fluoro-5-(trifluoromethyl)benzoic acid

In 2 lit four necked round bottom flask equipped with mechanical stirrer, thermometer, reflux condenser and an addition funnel, sodium hydroxide (63.5 g) and water (100 ml) was added and stirred for 15 mins at 25-35° C. To this solution, 3-fluoro-5-(trifluoromethyl)benzonitrile (100 g) was added, heated to 85-90° C. and stirred for 2 hrs at the same temperature. After completion of reaction, the reaction mass was allowed to cool to 25-35° C., acidified with aqueous hydrochloric acid and stirred for 30 mins at 25-35° C. The precipitated solid formed was filtered, washed with water, suck dried and then dried under vacuum at 50-55° C. for 6 hrs to get the title compound. Yield: 82 g.

Example 18: Preparation of 3-(4-methyl-imidazol-1-yl)-5-trifluoro methyl benzoic acid In 3 lit four necked round bottom flask equipped with mechanical stirrer, thermometer, reflux condenser and an addition funnel, 3-fluoro-5-(trifluoromethyl)benzoic acid (80 g), 4-methylimidazole (47.2 g) and dimethylacetamide (400 ml) was added, heated to 80-85° C. and stirred for 12 hrs at the same temperature. The reaction mass was cooled to room temperature, diluted with water (500 ml) and extracted with ethyl acetate (1000 ml). The solvent from organic layer was distilled off under vacuum and the obtained residue was titrated with water to get the title compound. Yield: 63 g.

Example-19: Preparation of Nilotinib

In 3 lit four necked round bottom flask equipped with mechanical stirrer, thermometer, reflux condenser and an addition funnel, 4-methyl-3-{[4-(3-pyridinyl)-2-pyrimidinyl]amino}benzoic acid (100 g) and N-methyl-2-pyrrolidone (750 ml) was added under nitrogen atmosphere at 25-35° C. and heated to 60-65° C. To this, thionylchloride (30 ml) was added at 60-65° C. and stirred for 3 hrs at the same temperature. After completion of reaction, a solution of 3-(4-methyl-1H-imidazol-1-yl)-5-(trifluoromethyl) aniline (86.6 g) in N-methyl-2-pyrrolidone (150 ml) was added to the reaction mass at 60-65° C. over a period of 45 mins. The reaction mass was further heated to 90-95° C. and stirred for 5 hrs at the same temperature. After completion of reaction, the reaction mass was cooled to 75-85° C. and water (1000 ml) was added to it over a period of 60 mins. Then reaction mass basified with aqueous sodium hydroxide solution at 75-85° C.; cooled to 35-45° C. and then stirred for 2 hrs. The reaction mass was further cooled to 5-10° C. and stirred for 3 hrs. The solid obtained was filtered, washed with water and dried under vacuum for 12 hrs at 60-65° C. to get the title compound. Yield: 145 g.

We claim:

1. A process for the preparation of a compound of Formula (I) or a pharmaceutically acceptable salt thereof,

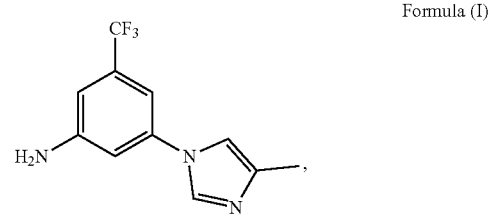 [SMILES: Cc1cn(-c2cc(N)cc(C(F)(F)F)c2)cn1]

Formula (I)

the process comprising:
a) reacting a compound of Formula (III) with 4-methyl imidazole in the presence of a base and optionally a suitable catalyst, in a solvent to obtain a compound of Formula (IV) or a pharmaceutically acceptable salt thereof,

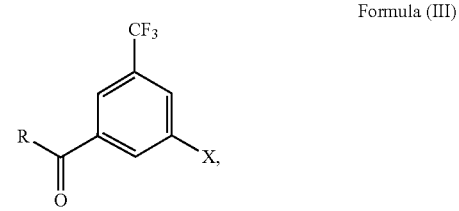

Formula (III)

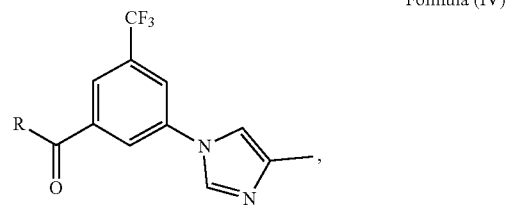

Formula (IV)

wherein "R" is —OH or —NH$_2$; and wherein "X" is a suitable group capable of forming a compound of Formula (IV);
b) converting the compound of Formula (IV), when "R" is —NH$_2$, to a compound of Formula (I) or a pharmaceutically acceptable salt thereof; or,
c) converting the compound of Formula (IV), when "R" is —OH, first to a compound of Formula (IV), wherein "R" is —NH$_2$, and then converting the resulted compound of Formula (IV), wherein "R" is —NH$_2$, to a compound of Formula (I) or a pharmaceutically acceptable salt thereof.

2. The process as claimed in claim 1, wherein "X" is selected from the group consisting of halides selected from chloride, bromide, iodide and fluoride; sulfonates selected from tosylate, mesylate, nosylate and triflate; and boronates selected from boronic acid and boronic acid pinacol ester.

3. The process as claimed in claim 1, wherein the suitable catalyst is selected from either copper salt in the presence of an additive, or a palladium catalyst optionally in the presence of an additional ligand.

4. The process as claimed in claim 3, wherein the suitable catalyst is 1,1'-Bis(diphenylphosphino)ferrocene-palladium (II)dichloride dichloromethane complex, or a combination of palladium diacetate and Bis[(2-diphenylphosphino) phenyl]ether, or a combination of 1,1'-Bis(diphenyl phosphino)ferrocene-palladium(II)dichloride dichloromethane complex and Bis[(2-diphenylphosphino) phenyl] ether.

5. The process as claimed in claim 1, wherein the suitable base is selected from the group consisting of inorganic bases selected from alkali metal hydroxides, alkali metal hydrides, alkali metal amides, alkali metal alkoxides, alkali metal carbonates, alkali metal bicarbonates, phosphates, ammonium carbonate; and organic bases.

6. The process as claimed in claim 5, wherein the base is selected from the group consisting of sodium hydroxide, potassium hydroxide, sodium hydride, sodium amide, potassium t-butoxide, sodium carbonate, potassium carbonate, trisodium phosphate, sodium bicarbonate, triethylamine, diisopropylamine and mixtures thereof.

7. The process as claimed in claim 1, wherein the solvent is selected form the group consisting of ketones selected from acetone, methyl ethyl ketone, methyl isobutyl ketone and diethyl ketone; nitriles selected from acetonitrile and propionitrile; ethers selected from diethyl ether, tetrahydrofuran, methyl tetrahydrofuran and 1,4-dioxane; esters selected from ethyl acetate, propyl acetate, isopropyl acetate, butyl acetate; polar aprotic solvent selected from dimethylacetamide, dimethylformamide, dimethylsulfoxide and N-methylpyrrolidone; water or mixtures thereof.

8. The process as claimed in claim 1, wherein the solvent is dimethylacetamide or dimethylsulfoxide.

9. The process as claimed in claim 1, wherein the step a) reaction is carried out at a temperature of about 75° C. to about 150° C.

10. The process as claimed in claim 1, wherein in the step b) the conversion of compound of Formula (IV) where R is —NH$_2$ to a compound of Formula (I) is carried out in presence of a halogen and a base or an alkali metal hypohalite.

11. The process as claimed in claim 10, wherein the halogen is selected from chlorine or bromine and the base is selected from sodium hydroxide, potassium hydroxide, sodium carbonate or potassium carbonate and the alkali metal hypohalite is sodium hypohalite.

12. The process as claimed in claim 11, wherein the step b) is carried out with bromine and sodium hydroxide.

13. The process as claimed in claim 1, wherein in the step c) the conversion of compound of Formula (IV), when "R" is —OH to a compound of Formula (IV), wherein "R" is —NH$_2$, is carried out by treating the compound of Formula (IV) with a suitable amine source in the presence of an activating agent and a solvent.

14. The process as claimed in claim 13, wherein the amine source is ammonia or ammonium hydroxide; and wherein the activating agent is selected from the group consisting of thionyl chloride, thionylbromide, oxalylchloride, oxalylbromide, phosphorous trichloride, phosphorous tribromide or phosphorous pentachloride.

15. The process as claimed in claim 1, wherein the compound of Formula (III), where "R" is —NH$_2$, is prepared by hydrolysing a nitrile compound of Formula (V),

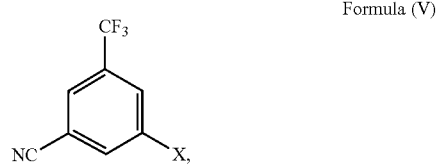

Formula (V)

with an acid, or with a peroxide reagent in the presence of a suitable base, wherein "X" is selected from the group consisting of a halogen selected from chloride, bromide, iodide or fluoride; sulfonates selected from tosylate, mesylate, nosylate, or triflate; or boronates selected from boronic acid or boronic acid pinacol ester.

16. The process as claimed in claim 15, wherein the acid is selected from one or more of the group consisting of hydrochloric acid, hydrobromic acid, sulphuric acid, acetic acid, formic acid, trifluoroacetic acid, methanesulfonic acid and mixtures thereof.

17. The process as claimed in claim 15, wherein the peroxide reagent is hydrogen peroxide or urea-hydrogen peroxide; and wherein the base is selected from the group consisting of sodium hydroxide, potassium hydroxide, lithium hydroxide, sodium carbonate, potassium carbonate, cesium carbonate, sodium bicarbonate or potassium bicarbonate.

18. The process as claimed in claim 15, wherein the peroxide reagent is hydrogen peroxide and the base is potassium carbonate.

19. The process as claimed in claim 15, wherein the reaction is carried out in the presence of a solvent selected from one or more of the group consisting of methanol, ethanol, isopropanol, butanol, t-butanol, acetone, methyl ethyl ketone, methyl isobutyl ketone, diethyl ketone, dimethylsulfoxide, diethyl ether, tetrahydrofuran, methyl tetrahydrofuran, water and mixtures thereof.

20. The process as claimed in claim 1, wherein the compound of formula (III) where R is —OH is prepared by hydrolysing a nitrile compound of Formula (V),

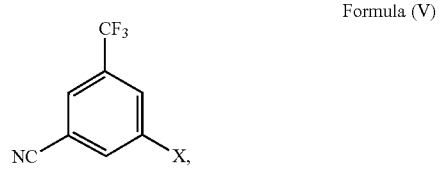

Formula (V)

with a suitable acid or a base; wherein "X" is selected from the group consisting of halogen selected from chloride, bromide, iodide or fluoride; sulfonates selected from tosylate, mesylate, nosylate, or triflate; or boronates selected from boronic acid or boronic acid pinacol ester.

21. The process as claimed in claim 20, wherein the suitable acid is selected from the group consisting of hydrochloric acid, hydrobromic acid, sulphuric acid, phosphoric acid or nitric acid; and wherein the base is selected from the group consisting of hydroxides selected from sodium hydroxide, potassium hydroxide, magnesium hydroxide, or calcium hydroxide; alkali metal alkoxides selected from sodium methoxide, sodium ethoxide, sodium t-butoxide; potassium t-butoxide; carbonates selected from sodium carbonate or potassium carbonate.

22. The process as claimed in claim 20, wherein the reaction is carried out in a solvent selected from one or more of the group consisting of polar aprotic solvent selected from dimethylacetamide, dimethylformamide, dimethylsulfoxide; alcohols selected from methanol, ethanol, butanol; nitriles selected from acetonitrile, propionitrile; water, or mixtures thereof.

23. The process as claimed in claim 20, wherein the reaction is carried out with sodium hydroxide in water.

24. A process for the preparation of nilotinib of Formula (II) or pharmaceutically acceptable salts thereof, Formula (II)

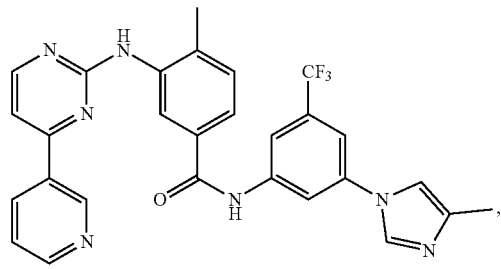

comprising:
a) reacting a compound of Formula (III) with 4-methyl imidazole in the presence of a base and optionally a suitable catalyst, in a solvent to obtain a compound of Formula (IV) or a pharmaceutically acceptable salt thereof, Formula (III)

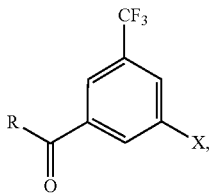

Formula (IV)

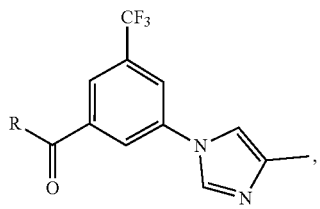

wherein "R" is —OH or —NH₂; and wherein "X" is a suitable group capable of forming a compound of Formula (IV);

b) converting the compound of Formula (IV), when "R" is —NH₂, to a compound of Formula (I) or a pharmaceutically acceptable salt thereof, Formula (I)

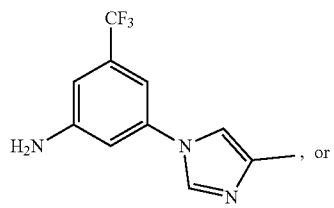

converting the compound of Formula (IV), when "R" is —OH, first to a compound of Formula (IV), wherein "R" is —NH₂, and then converting the resulted compound of Formula (IV), wherein "R" is —NH₂, to a compound of Formula (I) or a pharmaceutically acceptable salt thereof; and c) converting the compound of Formula (I) to the nilotinib or pharmaceutically acceptable salts thereof.

* * * * *